(12) United States Patent
Wallis et al.

(10) Patent No.: US 11,276,495 B2
(45) Date of Patent: Mar. 15, 2022

(54) SYSTEMS AND METHODS FOR PREDICTING MULTIPLE HEALTH CARE OUTCOMES

(71) Applicant: Cambia Health Solutions, Inc., Portland, OR (US)

(72) Inventors: Phillip Scott Wallis, Portland, OR (US); Daniel Jaesup Yoo, Portland, OR (US)

(73) Assignee: Cambia Health Solutions, Inc., Portland, OR (US)

( * ) Notice: Subject to any disclaimer, the term of this patent is extended or adjusted under 35 U.S.C. 154(b) by 511 days.

(21) Appl. No.: 16/033,006

(22) Filed: Jul. 11, 2018

(65) Prior Publication Data

US 2019/0019582 A1    Jan. 17, 2019

Related U.S. Application Data

(60) Provisional application No. 62/531,250, filed on Jul. 11, 2017.

(51) Int. Cl.
  *G16H 50/20* (2018.01)
  *G06N 3/04* (2006.01)
  *G06N 3/08* (2006.01)
  *G16H 50/50* (2018.01)

(52) U.S. Cl.
  CPC ............. *G16H 50/20* (2018.01); *G06N 3/04* (2013.01); *G06N 3/08* (2013.01); *G06N 3/082* (2013.01); *G06N 3/084* (2013.01); *G16H 50/50* (2018.01)

(58) Field of Classification Search
  CPC .......... G16H 50/20; G16H 50/50; G06N 3/04; G06N 3/08; G06N 3/082; G06N 3/084
  See application file for complete search history.

(56) References Cited

U.S. PATENT DOCUMENTS

| | | | |
|---|---|---|---|
| 2012/0221349 A1* | 8/2012 | Mora | G06Q 40/08 705/2 |
| 2014/0046693 A1* | 2/2014 | Wennberg | G16H 50/30 705/3 |
| 2017/0308787 A1* | 10/2017 | Corrado | G16H 50/20 |

FOREIGN PATENT DOCUMENTS

WO    WO-2017172629 A1 * 10/2017    ............. G06N 20/00

OTHER PUBLICATIONS

Mirtskhulava, et.al., Artificial Neural Network in Stroke Diagnosis, (2015), 17th UKSIM-AMSS International Conference on Modeling and Simulation, DOI 10.1109/UKSim.2015.33, pp. 50 53. (Year: 2015).*

Jiang et al. "Artificial Intelligence In Healthcare: Past, Present, and Future", Stroke and Vascular Neurology, (2017), doi:10.1136/svn-2017-000101, pp. 230-243. (Year: 2017).*

(Continued)

*Primary Examiner* — Robert A Sorey
*Assistant Examiner* — Kristine K Rapillo
(74) *Attorney, Agent, or Firm* — McCoy Russell LLP

(57) ABSTRACT

Systems and methods for predicting multiple health care outcomes are provided. In one embodiment, a method includes receiving clinical data relating to a patient, calculating, with a multi-tasking deep neural network model, a plurality of health outcomes for the patient based on the received clinical data, and displaying one or more of the plurality of health outcomes. In this way, the richness of health care data may be leveraged to predict multiple health care outcomes with a single predictive model.

18 Claims, 7 Drawing Sheets

(56) References Cited

OTHER PUBLICATIONS

Caruana, R., "Learning Many Related Tasks at the Same Time With Backpropagation," Proceedings of the 7th International Conference on Neural Information Processing Systems (NIPS'94), Nov. 28, 1994, Denver, Colorado, 8 pages.

Wolff, J et al., "Prevalence, Expenditures, and Complications of Multiple Chronic Conditions in the Elderly," Archives of Internal Medicine, vol. 162, No. 20, Nov. 11, 2002, 8 pages.

Hinton, G. et al., "Reducing the Dimensionality of Data with Neural Networks," Science, vol. 313, No. 5786, Jul. 28, 2006, 5 pages.

Collobert, R. et al., "A Unified Architecture for Natural Language Processing: Deep Neural Networks with Multitask Learning," Proceedings of the 25th International Conference on Machine Learning, Jul. 5, 2008, Helsinki, Finland, 8 pages.

Valderas, J. et al., "Defining Comorbidity: Implications for Understanding Health and Health Services," Annals of Family Medicine, vol. 7, No. 4, Jul. 2009, 7 pages.

Mikolov, T. et al., "Distributed Representations of Words and Phrases and their Compositionality," Proceedings of the 26th International Conference on Neural Information Processing Systems (NIPS'13), Dec. 5, 2010, Lake Tahoe, Nevada, 9 pages.

Bottou, L., "From Machine Learning to Machine Reasoning," Machine Learning, vol. 94, No. 2, Feb. 8, 2011, 15 pages.

Collobert, R. et al., "Natural Language Processing (Almost) from Scratch," Journal of Machine Learning Research, vol. 12. Aug. 2011, Available Online Feb. 2011, 45 pages.

Mikolov, T. et al., "Efficient Estimation of Word Representations in Vector Space," Proceedings of the International Conference on Learning Representations (ICLR 2013), May 2, 2013, Scottsdale, Arizona, 12 pages.

Bengio, Y. et al., "Better Mixing via Deep Representations," Proceedings of the 30th International Conference on Machine Learning, Jun. 16, 2013, Atlanta, Georgia, 9 pages.

Liu, X. et al., "Representation Learning Using Multi-Task Deep Neural Networks for Semantic Classification and Information Retrieval," Proceedings of the 2015 Conference of the North American Chapter of the Association for Computational Linguistics: Human Language Technologies, May 31, 2015, Denver, Colorado, 10 pages.

\* cited by examiner

SYSTEMS AND METHODS FOR PREDICTING MULTIPLE HEALTH CARE OUTCOMES

CROSS REFERENCE TO RELATED APPLICATIONS

The present application claims priority to U.S. Provisional Application No. 62/531,250, entitled "SYSTEMS AND METHODS FOR PREDICTING MULTIPLE HEALTH CARE OUTCOMES", and filed on Jul. 11, 2017. The entire contents of the above-listed application are hereby incorporated by reference for all purposes.

BACKGROUND/SUMMARY

In health care, there is a need to have a broad and rich predictive view of a person's health. Doctors and other medical professionals are trained to diagnose diseases and medical conditions by analyzing a patient's symptoms and data obtained from the patient's medical history and a physical examination. However, despite years of training and experience, doctors may not accurately diagnose a patient's medical condition, as many signs and symptoms are nonspecific. Furthermore, comorbidity of the condition with other medical conditions and/or the rareness of the condition, for example, may further obscure the true nature of the condition. Further still, the prediction of a patient's susceptibility to a particular disease or a particular medical condition proves even more challenging.

One approach to predictive health care is to train a machine learning model, such as a neural network, to predict or diagnosis a health condition. For example, a neural network may be trained with a large dataset containing the medical history of many patients with or without a particular health care outcome. To predict the susceptibility of a given patient to the particular health care outcome, similar data regarding the patient may be input to the trained neural network, which outputs a prediction.

To predict different outcomes, typical predictive modeling approaches would build a separate predictive model or system for each outcome. Building and maintaining a large number of predictive models is unwieldy. Furthermore, building separate models does not allow each model to support and bootstrap each other. It is well known that many health care outcomes share underlying causes and relationships. For example, diabetes is associated with kidney disease and cardiovascular disease. Building separate machine learning models makes it difficult for the different models to share information about underlying causes and factors.

Health care data is very rich and the large number of predictive features makes predictive models prone to overfitting to the training data. For example, there are tens of thousands of ICD diagnosis codes and similarly tens of thousands of different medical procedures. Predictive models that want to use the rich information stored in health care data are prone to the technical issue of overfitting.

Further still, many health care outcomes are rare, and thus data regarding such health care outcomes is sparse. Training models on very sparse data heightens the risk of overfitting problems. Since overfitting is a large concern in predicting health care outcomes, models are often constrained with heavy regularization or by limiting their expressiveness. For example, a neural network might be constrained to only one or two hidden layers with a small number of neurons. For neural networks, this reduces the expressive power of the network to map clinical data to health care outcomes.

The inventors herein have recognized the above issues and have devised several approaches to address them. In particular, systems and methods for predicting, for example simultaneously predicting, multiple health care outcomes are provided. In a first example embodiment, a method comprises: initializing a multi-tasking deep neural network comprising: an input layer comprising a plurality of input nodes; a plurality of hidden layers; a health care outcome masking layer; an output layer comprising a plurality of output nodes, wherein the plurality of output nodes correspond to a plurality of health care outcomes; and a health care outcome cost scaling layer; training the multi-tasking deep neural network using a training dataset; adjusting the health care outcome masking layer based on a characteristic of a patient; inputting patient clinical data into the input layer; predicting at least a first and a second health care outcome for the patient, the first health care outcome predicted based on a first output from a first output node, and the second health care outcome based on a second output from a second output node, wherein both the first and second output are based on the patient clinical data; and displaying one or more of the first and the second health care outcome. In this way, the large amount of available health care data may be leveraged to predict multiple health care outcomes for a patient using a single predictive model, while simultaneously reducing the risk of overfitting.

In another example embodiment, a method stored in a computer-readable storage medium of a computing system that when executed by a processor of the computing system performs the steps of: initializing a multi-tasking deep neural network comprising: an input layer comprising a plurality of input nodes; a plurality of hidden layers; a health care outcome masking layer; an output layer comprising a plurality of output nodes, wherein the plurality of output nodes correspond to a plurality of health care outcomes; and a health care outcome cost scaling layer; training the multi-tasking deep neural network using a training dataset comprising clinical data and corresponding health care outcomes; adjusting the health care outcome masking layer based on a physical characteristic of a patient; inputting patient clinical data into the input layer; predicting a plurality of patient health care outcomes based on output from the plurality of output nodes of the output layer; and displaying one or more of the predicted plurality of patient health care outcomes via a display subsystem of the computing system.

In another example embodiment, a computing system comprises: a display subsystem; a processor; and a computer-readable storage medium containing instructions that when executed by the processor perform the steps of: initializing a multi-tasking deep neural network comprising: an input layer comprising a plurality of input nodes; a plurality of hidden layers; a health care outcome masking layer comprising a plurality of masking nodes; an output layer comprising a plurality of output nodes corresponding to a plurality of health care outcomes; and a health care outcome cost scaling layer, wherein the health care cost scaling layer adjusts a weight of an error associated with each of the plurality of output nodes; training the multi-tasking deep neural network using a training dataset comprising clinical data; adjusting the health care outcome masking layer based on a physical characteristic of a patient; inputting patient clinical data into the plurality of input nodes; predicting a plurality of patient health care outcomes based on output from the plurality of output nodes, wherein the plurality of patient health care outcomes comprise classification and regression health care outcomes; and displaying one or more of the plurality of patient health care outcomes.

The above summary is provided to introduce a selection of concepts in a simplified form that are further described below in the Detailed Description. This summary is not intended to identify key features or essential features of the subject matter, nor is it intended to be used to limit the scope of the subject matter. Furthermore, the subject matter is not limited to implementations that solve any or all of the disadvantages noted above or in any part of this disclosure.

DETAILED DESCRIPTION

Figure 2:
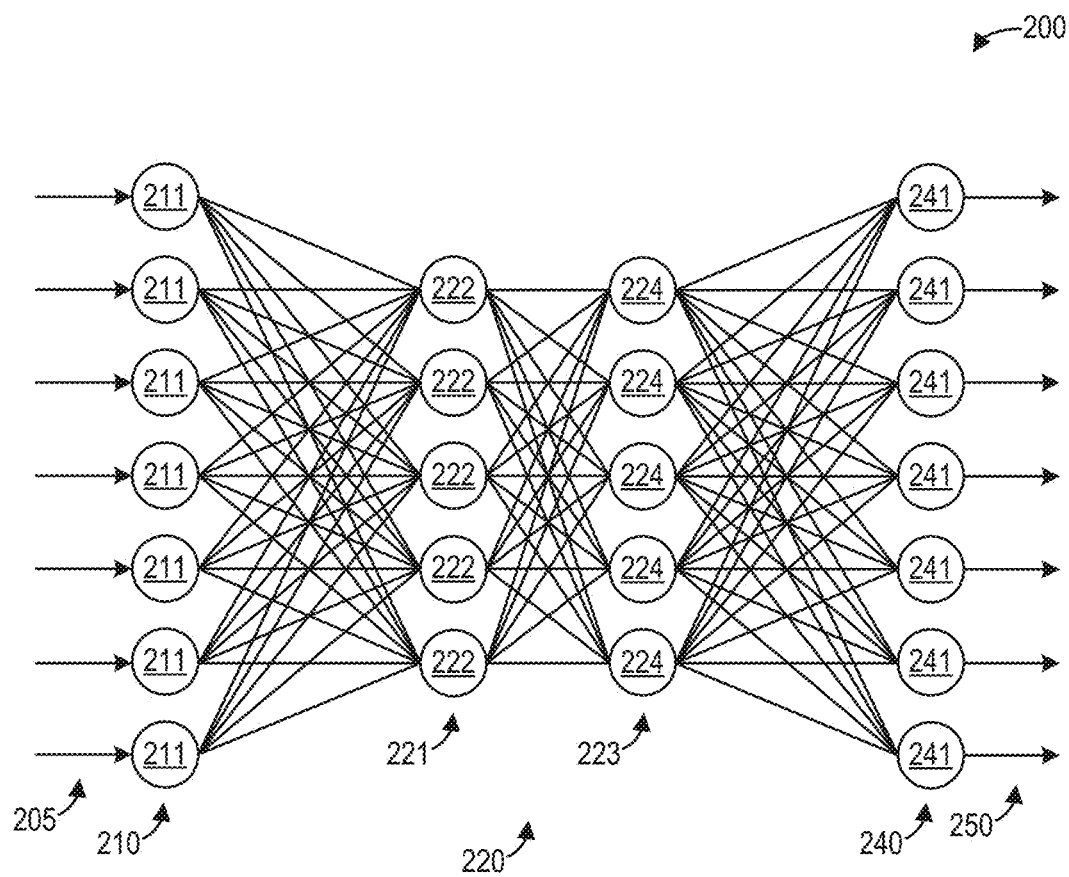
FIG. 2 shows a high-level diagram illustrating an example multi-tasking deep neural network.
Figure 3:
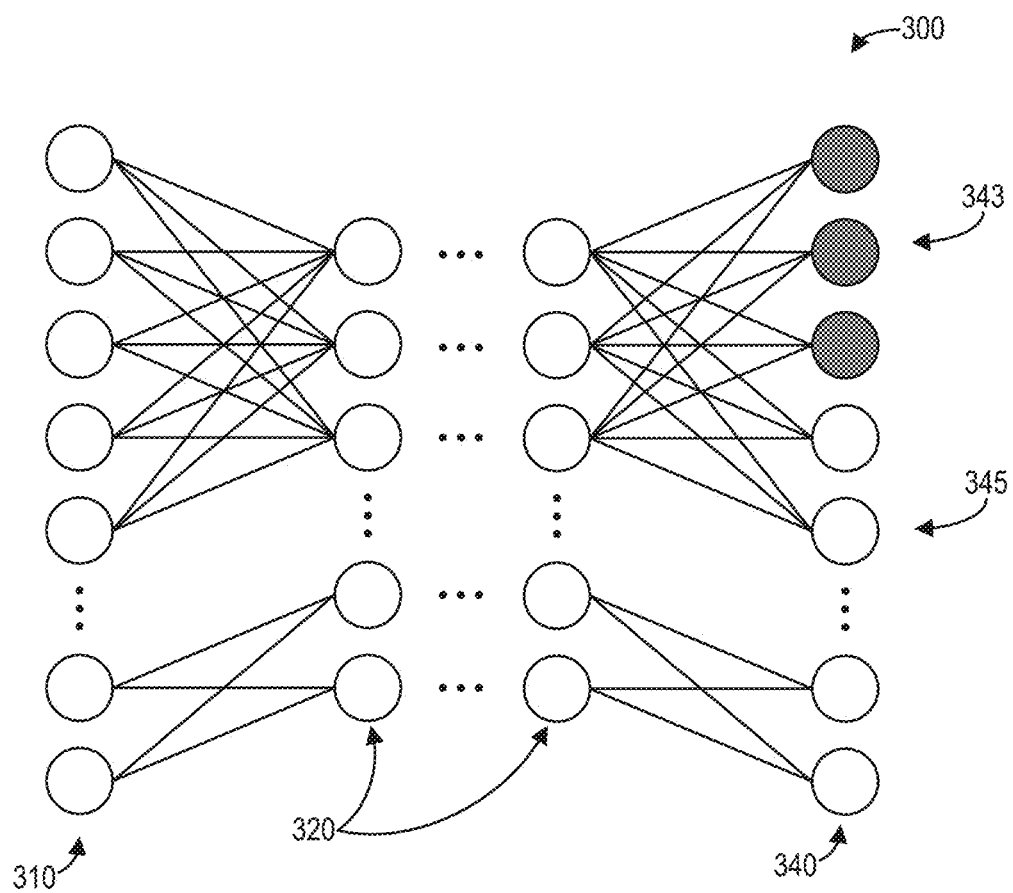
FIG. 3 shows a high-level diagram illustrating an example multi-tasking deep neural network that predicts both classification and regression health care outcomes.
Figure 4:
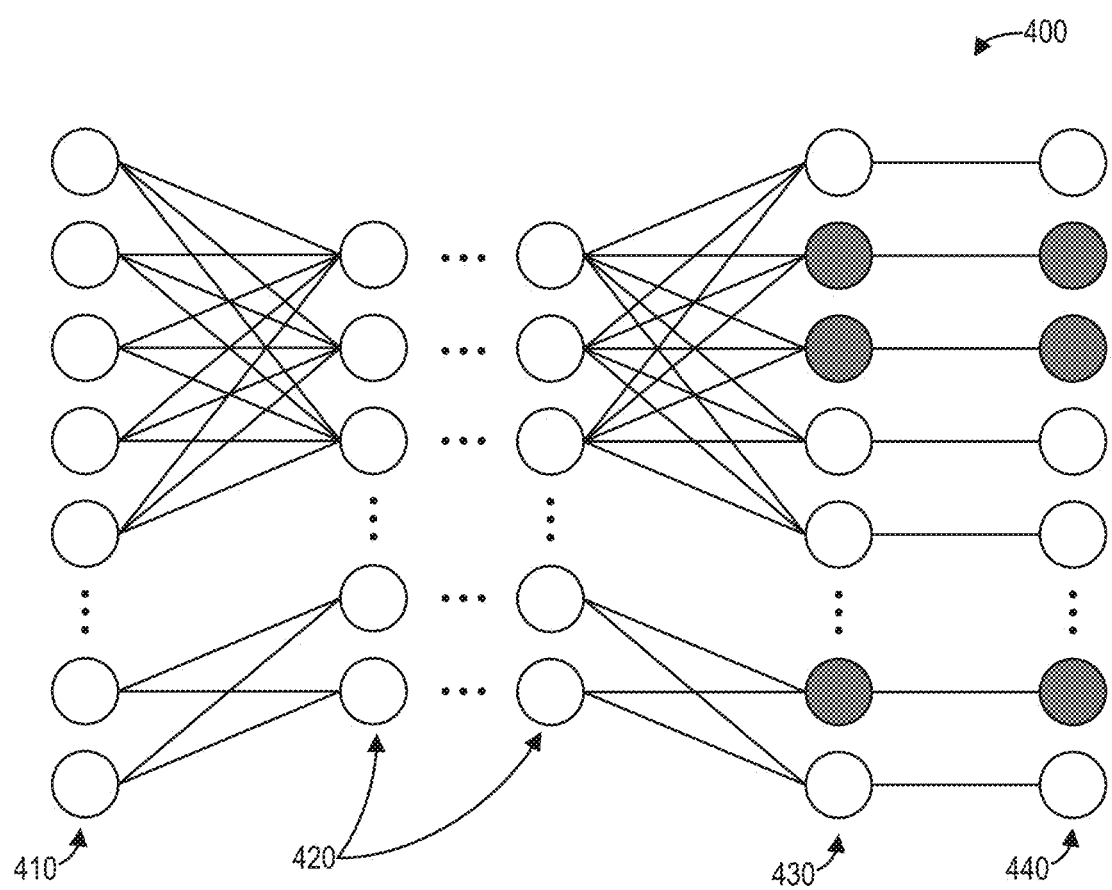
FIG. 4 shows a high-level diagram illustrating an example multi-tasking deep neural network that includes a health care outcome masking layer.
Figure 5:
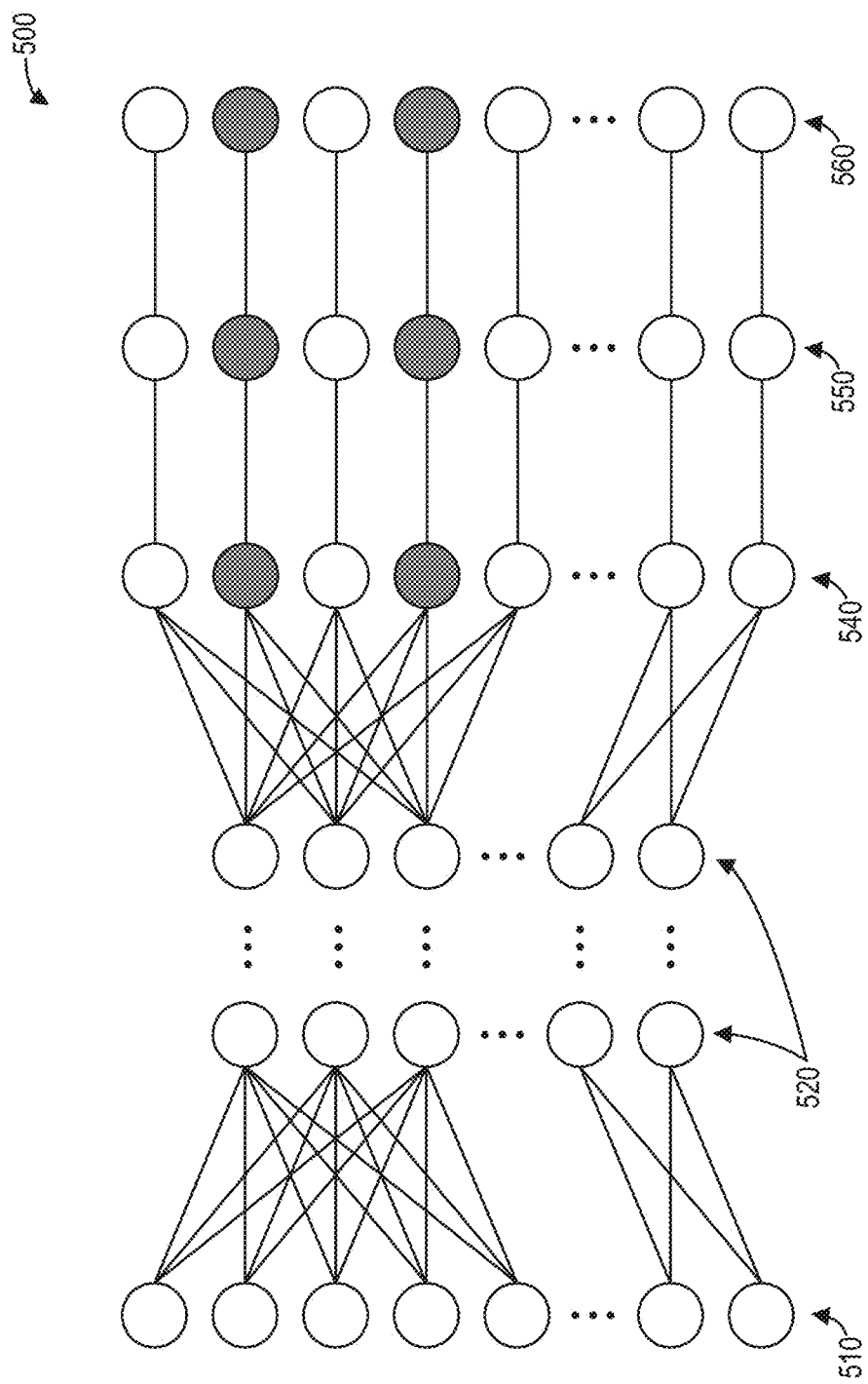
FIG. 5 shows a high-level diagram illustrating an example multi-tasking deep neural network that includes a health care outcome masking layer and a health care outcome cost-scaling layer.

The present description relates to systems and methods for predicting multiple health care outcomes. In particular, systems and methods are provided for predicting multiple health care outcomes with a multi-tasking deep neural network. A multi-tasking deep neural network may be implemented on a computing system, such as the computing system depicted in FIG. 1. The multi-tasking deep neural network includes a plurality of input nodes and a plurality of output nodes, as depicted in FIG. 2. In some examples, the multi-tasking deep neural network may be specially configured to predict both classification and regression health care outcomes, as depicted in FIG. 3. A multi-tasking deep neural network may include a health care outcome masking layer to suppress prediction of irrelevant health care outcomes, as depicted in FIG. 4. In some examples, a multi-tasking deep neural network may also include a health care outcome cost-scaling layer, as depicted in FIG. 5. In one example, a method for predicting multiple health care outcomes with a multi-tasking deep neural network, such as the method depicted in FIG. 6, may include initializing a multi-tasking deep neural network, preparing clinical data for training the model, training the model with the prepared clinical data, and then predicting multiple health care outcomes with the trained multi-tasking deep neural network. In another example, a method for predicting multiple health care outcomes with a multi-tasking deep neural network, such as the method depicted in FIG. 7, may include initializing a multi-tasking deep neural network, training the multi-tasking deep neural network using a training dataset, adjusting the health care outcome masking layer based on a characteristic of a patient, inputting patient clinical data into the input layer, predicting at least a first and a second health care outcome for the patient, and displaying one or more of the first and the second health care outcome. In some examples, the systems are approaches are configured to address specific technical issues unique to the particular type of health care data described herein, particularly with regard to computational efficiency in improving the ability to handle data structures with overfitting.

Figure 1:
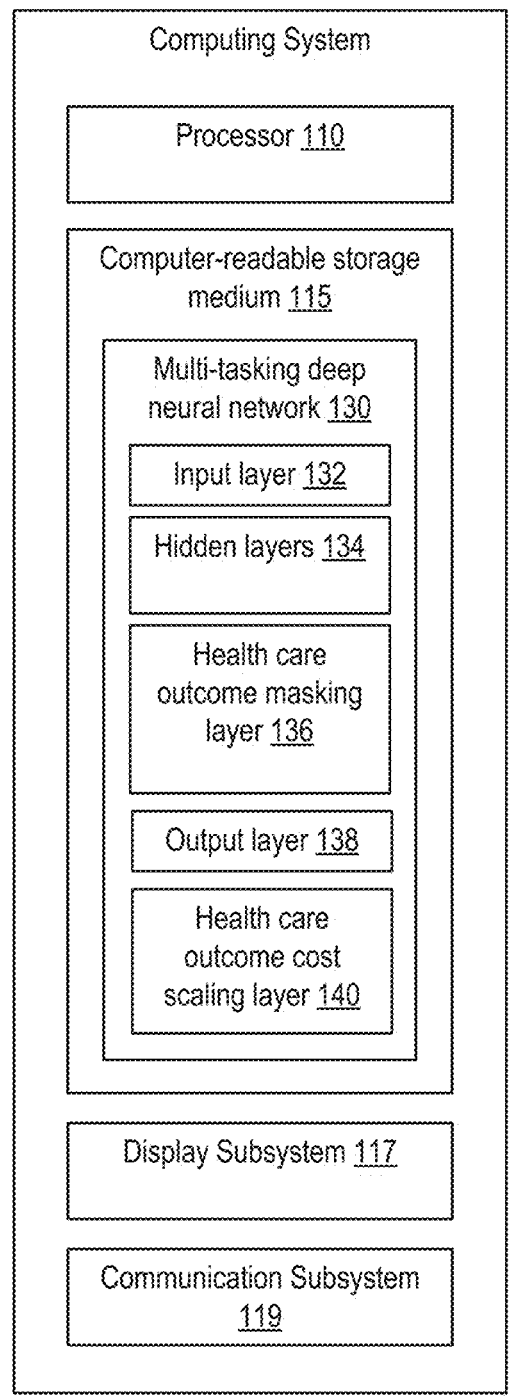
FIG. 1 shows a block schematic diagram of an example computing system for predicting multiple health care outcomes.

FIG. 1 schematically shows a non-limiting computing system 100 that may perform one or more of the methods and processes described herein. It is to be understood that virtually any computer architecture may be used for a computing system without departing from the scope of this disclosure. In different embodiments, computing system 100 may take the form of a mainframe computer, server computer, desktop computer, laptop computer, tablet computer, network computing device, mobile computing device, mobile communication device, and so on.

Computing system 100 includes a processor 110 and a computer-readable storage medium 115. Computing system 100 may include a display subsystem 117, communication subsystem 119, and/or other components not shown in FIG. 1. For example, computing system 100 may also optionally include user input devices such as keyboards, mice, cameras, microphones, and/or touch screens.

Processor 110 may include one or more physical devices configured to execute one or more instructions. For example, processor 110 may be configured to execute one or more instructions that are part of one or more applications, services, programs, routines, libraries, objects, components, data structures, or other logical constructs. In one example, processor 110 may execute one or more methods described herein, such as method 600 and 700 discussed in reference to FIGS. 6 and 7 below. Such instructions may be implemented to perform a task, implement a data type, transform the state of one or more devices, or otherwise arrive at a desired result.

Processor 110 may include one or more processors that are configured to execute software instructions. Additionally or alternatively, the processor 110 may include one or more hardware and/or firmware logic machines configured to execute hardware and/or firmware instructions. Processors of the processor 110 may be single core or multi-core, and the programs executed thereon may be configured for parallel or distributed processing. The processor 110 may optionally include individual components that are distributed throughout two or more devices, which may be remotely located and/or configured for coordinated processing. One or more aspects of the processor 110 may be virtualized and executed by remotely-accessible networked computing devices configured in a cloud computing configuration.

Computer-readable storage medium 115 may include one or more physical, non-transitory devices configured to hold data and/or instructions executable by the processor 110 to implement the herein described methods and processes. When such methods and processes are implemented, the state of the computer-readable storage medium may be transformed (for example, to hold different data).

Computer-readable storage medium 115 may include removable media and/or built-in devices. Computer-readable storage medium 115 may include optical memory (for example, CD, DVD, HD-DVD, Blu-Ray Disc, etc.), and/or magnetic memory devices (for example, hard disk drive, floppy disk drive, tape drive, MRAM, etc.), and the like. Computer-readable storage medium 115 may include devices with one or more of the following characteristics: volatile, nonvolatile, dynamic, static, read/write, read-only, random access, sequential access, location addressable, file addressable, and content addressable. In some embodiments, processor 110 and computer-readable storage medium 115 may be integrated into one or more common devices, such as an application specific integrated circuit or a system on a chip.

It is to be appreciated that the computer-readable storage medium 115 includes one or more physical, non-transitory devices. In contrast, in some embodiments aspects of the instructions described herein may be propagated in a transitory fashion by a pure signal (for example, an electromagnetic signal, an optical signal, etc.) that is not held by a physical device for at least a finite duration. Furthermore, data and/or other forms of information pertaining to the present disclosure may be propagated by a pure signal.

Computer-readable storage medium 115 may have instructions stored therein for implementing multi-tasking deep neural network 130. Routines/methods for initializing, training, and adjusting parameters of multi-tasking deep neural network 130 may also be stored in computer-readable storage medium 115 (not shown). Multi-tasking deep neural network 130 comprises input layer 132, a plurality of hidden layers 134, health care outcome masking layer 136, output layer 138, and health care outcome cost scaling layer 140. Computer-readable storage medium 115 may store the various components of multi-tasking deep neural network 130 in separate locations within storage medium 115, wherein the locations store one or more parameters associated with the corresponding component of the multi-tasking deep neural network 130. In one example, hidden layers 134 may comprise functions mapping input and output for each of the plurality of nodes comprising the plurality of hidden layers 134, wherein the output of each node of the plurality of hidden layers 134 comprise an adjustable weight associated with the output. In another example, at health care outcome masking layer 136, may comprise parameters for each of the plurality of masking nodes of health care outcome masking layer 136. As an example, each of the nodes of health care outcome masking layer may transform inputs into outputs by multiplying by either zero (for masked/suppressed health care outcomes) or one (for unmasked/not suppressed health care outcome), and these parameters may be stored at health care outcome masking layer 136. In another example, the error (difference between predicted health care outcome and actual health care outcome) for each of the plurality of output nodes may be recorded at output layer 138, and used in conjunction with a training routine to adjust the plurality of weights associated with the plurality of nodes of hidden layers 134. In yet another example, health care outcome cost scaling layer 140, which comprises a plurality scaling nodes, each of which receives input from a corresponding output node of output layer 138, (that is, there is a one to one mapping of each output node to each health care cost scaling node, such that n output nodes and n health care cost scaling nodes form n unique pairs) may store parameters associated with the plurality of health care cost scaling nodes at health care cost scaling layer 140, wherein the parameters are used to adjust a weight of an error calculated for a health care outcome predicted by a given output node of output layer 138. In other examples, the parameters associated with multi-tasking deep neural network 130 may be stored in substantially a single location within computer-readable storage medium 115. In a further example, the parameters associated with multi-tasking deep neural network 130 may be stored in different computing systems connected in a network.

When included, display subsystem 117 may be used to present a visual representation of data held by computer-readable storage medium 115. As the herein described methods and processes change the data held by the computer-readable storage medium 115, and thus transform the state of the computer-readable storage medium 115, the state of display subsystem 117 may likewise be transformed to visually represent changes in the underlying data. Display subsystem 117 may include one or more display devices utilizing virtually any type of technology. Such display devices may be combined with processor 110 and/or computer-readable storage medium 115 in a shared enclosure, or such display devices may be peripheral display devices.

When included, communication subsystem 119 may be configured to communicatively couple computing system 100 with one or more other computing devices. Communication subsystem 119 may include wired and/or wireless communication devices compatible with one or more different communication protocols. As non-limiting examples, communication subsystem 119 may be configured for communication via a wireless telephone network, a wireless local area network, a wired local area network, a wireless wide area network, a wired wide area network, etc. In some embodiments, communications subsystem 119 may allow computing system 100 to send and/or receive messages to and/or from other devices via a network such as the public Internet.

FIG. 2 shows a high-level diagram illustrating an example architecture of a multi-tasking deep neural network 200. Multi-tasking deep neural network 200 uses a shared representation to predict a plurality of health care outcomes based on a plurality of clinical data comprised of health care input features (in one example health care input features may comprise diagnosis codes, and/or aspects of patient medical history). Multi-tasking deep neural network 200 is described herein with regard to the systems and components of FIG. 1, though it should be appreciated that the multi-tasking deep neural network may be implemented with other systems and components without departing from the scope of the present disclosure. As a non-limiting example, multi-tasking deep neural network 200 may be stored in a computer-readable storage medium 115 and may be updated, executed, or otherwise processed via processor 110.

Multi-tasking deep neural network 200 includes an input layer 210, a plurality of hidden layers 220 including a first hidden layer 221 and a second hidden layer 223, and an output layer 240. Each layer 210, 221, 223, and 240 includes a plurality of nodes, depicted as circles in FIG. 2. Specifically, input layer 210 includes a plurality of input nodes 211, first hidden layer 221 includes a plurality of hidden nodes 222, second hidden layer 223 includes a plurality of hidden nodes 224, and output layer 240 includes a plurality of output nodes 241. In one example the hidden nodes 222 and 224 comprise artificial neurons (herein also referred to as nodes) with non-linear activation functions that map weighted inputs to the output.

To predict multiple health care outcomes, a plurality of clinical data input features 205 are input to the multi-tasking deep neural network 200 which in turn outputs a plurality of health care outcomes corresponding to the output nodes 241 of outputs 250. More specifically, each input feature 205 is input to a corresponding input node 211 of the input layer 210. Each input node 211 is connected to each hidden node 222 of the first hidden layer 221, as depicted by the lines connecting the input layer 210 to the first hidden layer 221. Each hidden node 222 of the first hidden layer 221 is connected to each hidden node 224 of the second hidden layer 223. Each hidden node 224 is connected to each output node 241 of the output layer 240. Each output node 241 of the output layer 240 outputs to a corresponding node of outputs 250.

In one example, the hidden nodes receive one or more inputs and sum them to produce an output. The sums of each node are weighted, and the sum is passed through a non-linear activation function. The resulting output may then be passed on to each node in the following layer.

Multi-tasking deep neural network 200 may therefore comprise a feedforward neural network. In some examples, the multi-tasking deep neural network 200 may be trained through backpropagation. To minimize total error, gradient descent may be used to adjust each weight in proportion to the derivative of the error with respect to that weight. In another example, global optimization methods may be used to train the weights of the neural network 200.

It should be appreciated that, for simplicity, FIG. 2 illustrates a relatively small number of nodes, and that in practice the multi-tasking deep neural network 200 may include many thousands of nodes. As an example, while seven input nodes 211 are depicted in the input layer 210, in some examples the input layer 210 may include thousands of input nodes 211. In one example, the input layer 210 may include as many as 2,800 input nodes 211, each input node 211 configured to receive one input feature 205 or data variable.

Moreover, although the multi-tasking deep neural network 200 is depicted as including two hidden layers 221 and 223, it should be appreciated that the multi-tasking deep neural network 200 may include from two to x hidden layers, where x is a positive integer greater than two. However, empirical results indicate that two hidden layers is a reasonable architecture.

Further, the number of hidden nodes 222 in hidden layer 221 and the number of hidden nodes 224 in hidden layer 223 is optimizable. For example, the number of hidden nodes may be based on the number of outputs or output nodes 241. As an illustrative example, for a neural network model with two output nodes 241, the optimal number of hidden nodes in the hidden layers 220 may comprise two hundred hidden nodes. For two hidden layers 221 and 223, the two hundred hidden nodes may, in some examples, be distributed equally between the hidden layers such that the hidden layers have the same width. For example, hidden layer 221 may include one hundred hidden nodes 222 while hidden layer 223 may include one hundred hidden nodes 224. In contrast, for thirty output nodes 241, the optimal number of hidden nodes in the hidden layers 220 may comprise nine hundred hidden nodes. In this example, the hidden nodes may be distributed equally across the hidden layers 220, such that hidden layer 221 includes four-hundred-fifty hidden nodes 222 while hidden layer 223 includes four-hundred-fifty hidden nodes 224. Similarly, as the number of output nodes 241 in the output layer 240 is increased, the optimal number of hidden nodes may also increase.

Although constructing hidden layers with equal widths or equal numbers of hidden nodes may comprise a simplest architecture for the neural network model, it should be appreciated that in some examples, the number of hidden nodes in each hidden layer 220 may be different, such that the widths of the hidden layers are also different.

The multi-tasking deep neural network 200 is trained to simultaneously predict a plurality of health care outcomes corresponding to outputs 250. Medical claims data and other bioinformatics corresponding to a patient and patient medical history may be used as input features 205. To train the neural network 200, claims data and other medical data for a plurality of patients is input to the neural network 200 via the plurality of input nodes 211. The health care outcomes for this training data is known, and so the weights of the nodes of the hidden layers 220 are adjusted (such as through backpropagation, or other optimization methods known in the art, as discussed above) such that the outputs 250 comprise the known outcomes. Hidden layers 220 thus comprise a shared representation.

Outputs 250, which correspond to health care outcomes, may comprise two categories. The first of these categories is called a classification health care outcome, which comprises a binary (yes or no) output corresponding to a type of health care outcome. In one example, a classification health care outcome may comprise if an inpatient stay at a hospital is predicted in the next 6 months, wherein a "yes" output from an output node of outputs 250 corresponding to this health care outcome may indicate that an inpatient stay for a given patient is likely at a time within the next six months. The second category of health care outcomes is called a regression health care outcome, and comprises a non-binary output from an output node of the plurality of output nodes 241. In one example, a regression health care outcome comprises a functional transformation of input to output, such as by transformation of input to output by passing the input through a linear function. Regression health care outcomes are able to answer questions for which a binary (yes or no) response may not be sufficient. In one example, a regression health care outcome may comprise a duration of an inpatient stay at a hospital, such as by predicting that the inpatient stay will last for 2 days. In another example, a regression health care outcome may comprise a prediction of a monetary cost associated with predicted medical procedures, such as a prediction that over the next year a patient may require $5,482 worth of medical procedures.

In some examples, the multi-tasking deep neural network may be configured to simultaneously perform both classification and regression for multiple outcomes. FIG. 3 shows a high-level diagram illustrating an example architecture for a multi-tasking deep neural network 300 that simultaneously performs classification and regression for multiple outcomes. Similar to the multi-tasking deep neural network 200 described above, multi-tasking deep neural network 300 includes an input layer 310, a plurality of hidden layers 320, and an output layer 340.

In addition, at least one or more of the output nodes of the output layer 340 comprise classification output nodes 343, while the remaining output nodes of the output layer 340 comprise regression output nodes 345.

The deep multi-tasking deep neural network model allows one to build and train a model to predict both classification and regression outcomes simultaneously. The neural network model back-propagates costs for both the classification and regression outcomes.

When building a model to predict multiple outcomes in the health care domain, it is common for some outcomes to only apply to certain individuals based on physical characteristics of the patient. For example, one may not want to predict testicular cancer for females based on the physical characteristic of sex. In order to train a model to predict many health care outcomes, including those that only apply to certain segments of the population, the neural network may include a health care outcome masking layer that masks certain outcomes from populations they do not apply to, and in addition, such health care outcome masking/suppression may be implemented when predicting health care outcomes for a patient based on characteristics of that patient precluding certain health care outcomes.

FIG. 4 shows a high-level diagram illustrating an example architecture for a multi-tasking deep neural network 400 that includes a health care outcome masking layer. Multi-tasking deep neural network 400 includes an input layer 410, a plurality of hidden layers 420, a health care outcome masking layer 430, and an output layer 440. As illustrated in FIG. 4, nodes of health care outcome masking layer 430 which are darkened represent masking nodes outputting zero, and thus suppressing a given health care outcome associated with a corresponding output node of output layer 440 (where the corresponding output node is also darkened to illustrate the suppressed output), while undarkened nodes of health care masking layer 430 represented masking nodes which multiply their input by one, and thus do not suppress prediction of an associated health care outcome of an associated output node.

The health care outcome masking layer 430 enables the training of a model on different health care outcomes that apply to different segments of the population. The health care outcome masking layer 430 masks (also referred to herein as suppressing) irrelevant outcomes by multiplying by zero and preventing costs from backpropagating. The health care outcome masking layer 430 thus enables the hidden layers to be trained with all input features to develop the shared representation while minimizing output of irrelevant outcomes.

As an illustrative example, for prediction of avoidable emergency room (ER) visits, the health care outcome masking layer 430 may mask outputs for patients under the age of one, since such a prediction is irrelevant for such patients. As another example, the health care outcome masking layer 430 may mask a certain age range for osteoporosis and bone fractures. As yet another example, testicular cancer is only a risk for male patients, and so the health care outcome masking layer 430 may mask predictions and training gradients for testicular cancer in female patients.

Adding a health care outcome cost scaling layer to the architecture can aid proper training of the neural network. Herein, cost refers to a weight of an error associated with a given health care outcome (and the output node associated with said outcome). Scaling the costs is important for preventing the multi-tasking deep neural network from being dominated by more common health care outcomes at the expense of prediction accuracy for less common, or more rare, health care outcomes. In other words, the health care outcome cost scaling layer, by adjusting the weights of error associated with each of the output nodes of the output layer, enables a balance of prediction accuracy amongst all health care outcomes to be maintained, even when a training data set is unevenly distributed amongst the possible health care outcomes. If a health care outcome has very high costs, the network will tend to focus on optimizing performance for the high cost health care outcome. A health care outcome cost scaling layer can be used to make the costs reflect real-world estimates of the true costs (in one example, a real-world cost being an impact to quality of life) or to scale the costs to counter balance the unevenly distributed clinical training data.

FIG. 5 shows a high-level diagram illustrating an example architecture for a multi-tasking deep neural network 500 that includes a health care outcome masking layer and a health care outcome cost-scaling layer. Multi-tasking deep neural network 500 includes an input layer 510, a plurality of hidden layers 520, a health care outcome masking layer 540, an output layer 550, and a health care outcome cost-scaling layer 560. As illustrated in FIG. 5, nodes of health care outcome masking layer 540 which are darkened represent masking nodes outputting zero, and thus suppressing a given health care outcome associated with a corresponding output node of output layer 550 and scaling node of health care outcome scaling layer 560 (where the corresponding output node and scaling node is also darkened to illustrate the suppressed output), while undarkened nodes of health care masking layer 540 represented masking nodes which multiply their input by one, and thus do not suppress prediction of an associated health care outcome of an associated output node.

The health care outcome cost-scaling layer 560 scales costs so that regression and classification health care outcomes have similar scales. Classification costs are scaled to reflect the relative real-world cost of making errors or to balance the cost of a mean probability prediction across rare and common health care outcomes.

It should be noted that the term "cost" as defined herein is used in the sense of mathematical optimization and machine learning rather than an economic cost.

Figure 6:
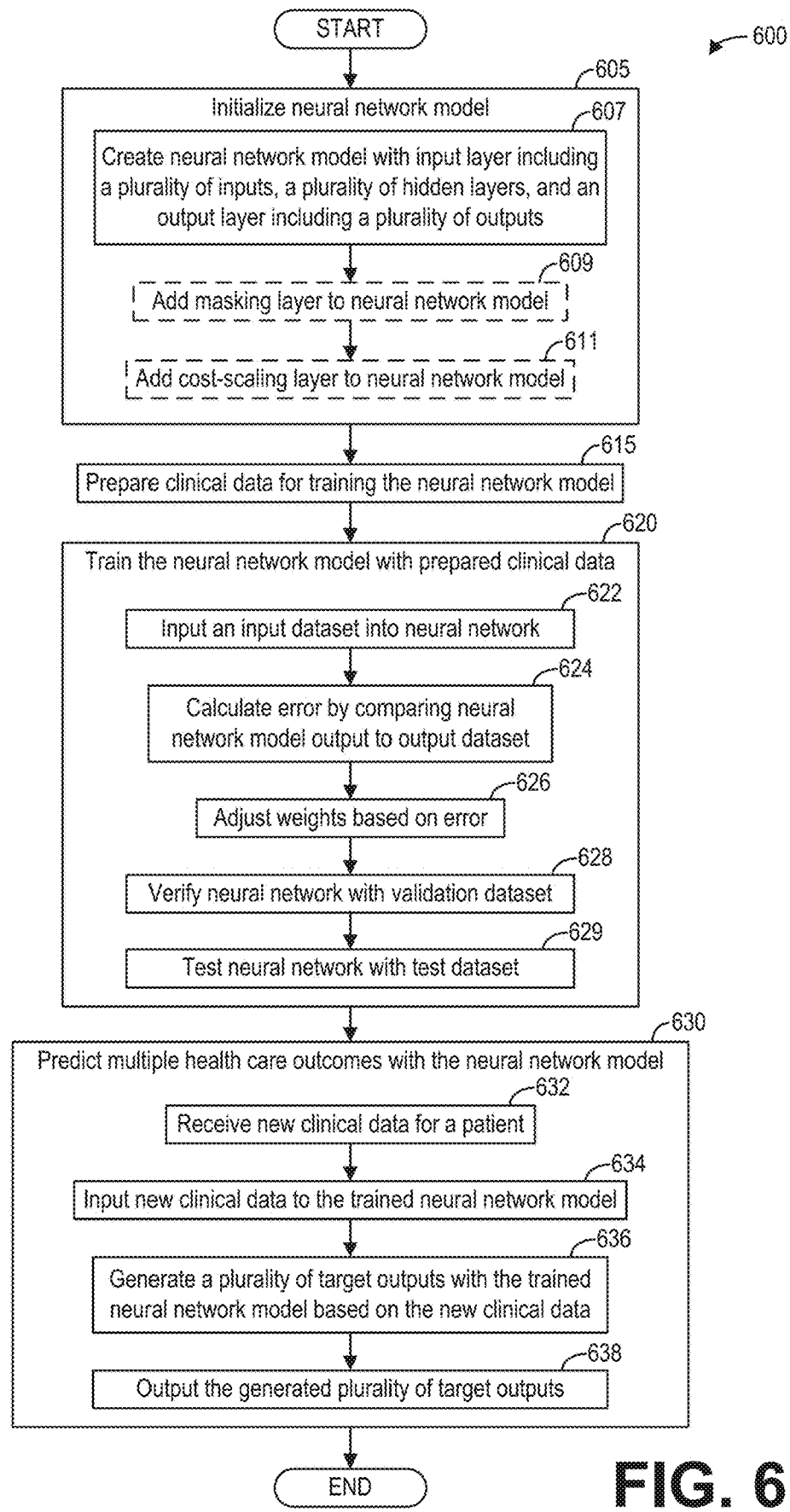
FIG. 6 shows a high-level flow chart illustrating an example method for predicting multiple health care outcomes with a multi-tasking deep neural network.

FIG. 6 shows a high-level flow chart illustrating an example method 600 for predicting multiple health care outcomes with a multi-tasking deep neural network. Method 600 may be carried out, as a non-limiting example, by a computing system such as the computing system described herein above with regard to FIG. 1, though it should be understood that the method may be carried out by other systems without departing from the scope of the current disclosure.

Method 600 begins at 605. At 605, method 600 includes initializing a multi-tasking deep neural network. At 607, initializing the multi-tasking deep neural network includes creating a multi-tasking deep neural network with an input layer including a plurality of inputs, a plurality of hidden layers comprising a plurality of hidden nodes in each of the plurality of hidden layers, and an output layer including a plurality of outputs. Each node or neuron of the layers may be initialized with an initial weight. During training of the multi-tasking deep neural network, the initial weight is adjusted based on the training data, as discussed further herein.

At 609, initializing the multi-tasking deep neural network includes adding a health care outcome masking layer to the neural network model. The health care outcome masking layer masks out predictions and training gradients for populations where a health care outcome does not apply. For example, testicular cancer is only a risk for male patients, and so the health care outcome masking layer may mask testicular cancer predictions for female patients. In some examples, the health care outcome masking layer may be added between the hidden layers and the output layer, as depicted in FIG. 4.

At 611, initializing the multi-tasking deep neural network includes adding a health care outcome cost-scaling layer to the neural network model. A health care outcome cost-scaling layer may scale the relative value of the costs in order to prevent the domination of the multi-tasking deep neural network by more common outcomes. In this way, rare health outcomes can take advantage of sharing a representation with more common health outcomes. If the health care outcomes themselves have an identified relative importance (such as an monetary cost associated with the health care outcome, or an impact to quality of life associated with the health care outcome), the costs can be scaled according to relative importance. In the absence of a defined relative importance, the cost of a mean prediction can be used to scale the costs to be comparable across health care outcomes. In one example, uneven distribution of training data across the space of possible health care outcomes may be compensated for by increasing a weight associated with a less common/more rare health care outcome. In some examples, the health care outcome cost-scaling layer may be added after the output layer of the neural network model, as depicted in FIG. 5.

After initializing the multi-tasking deep neural network model, method 600 continues to 615. At 615, method 600 includes preparing clinical data for training the multi-tasking deep neural network. Preparing clinical data for training may comprise, as illustrative and non-limiting examples, cleansing the data, wrangling the data, and dividing the data into data subsets. The clinical data may be retrieved locally from memory, for example from computer-readable storage medium 115. Additionally or alternatively, the clinical data may be retrieved from a remote storage device, for example via communication subsystem 119, and at least temporarily loaded into local memory in computer-readable storage medium 115.

Cleansing the data may comprise, for example, detecting and correcting corrupt records in the raw clinical data. For example, the method may identify incomplete, inaccurate, or irrelevant portions of each record in the raw clinical data, and then replace, modify, or delete the identified data.

Wrangling the data may comprise, for example, mapping the raw or cleansed data into a standardized format or data structure suitable for input to the neural network model. The standardized format or data structure may comprise a universal data structure that accommodates all types of information present in all records of the raw clinical data.

In some examples, the raw clinical data may first be wrangled into an appropriate data structure, and then cleansed. For example, some records of the clinical data may not include the same type of information as other records of the clinical data. Therefore, each record may be mapped to a universal data structure that accommodates all types of information present in all records. After wrangling the data, some of the wrangled records may be incomplete; that is, some records may include missing data. The wrangled records may therefore be cleansed in order to replace the missing data or null values with default values. It should be appreciated that in some examples, the raw clinical data may be cleansed prior to wrangling.

In some examples, the clinical data may be divided into data subsets, including one or more of a learning data subset, a validation data subset, and a testing data subset. The learning data subset may be used to train or fit the model, the validation data subset may be used to verify the model, and the testing data subset may be used for testing the usability or accuracy of the model.

The method may randomly divide the clinical data into the data subsets. As an illustrative example, 50% of the clinical data may be designated as the training data subset, 25% of the clinical data may be designated as the validation data subset, and 25% of the clinical data may be designated as the testing data subset, though it should be appreciated that different percentages of the clinical data may be designated to one of the data subsets.

The method may further subdivide the clinical data into input datasets and corresponding output datasets. Training the multi-tasking deep neural network, as discussed further herein, may thus include adjusting the weights of the multi-tasking deep neural network such that the inputs of the input datasets yield the corresponding outputs of the output datasets.

Continuing at 620, method 600 includes training the multi-tasking deep neural network with the prepared clinical data. Training the multi-tasking deep neural network with the prepared clinical data may comprise, for example, training the multi-tasking deep neural network initialized at 605. For example, at 622, method 600 may input an input dataset into the multi-tasking deep neural network. At 624, method 600 may calculate an error by comparing the multi-tasking deep neural network output to an output dataset comprising health care outcomes corresponding to the clinical data. At 626, method 600 may adjust the weights of the hidden layers based on the error.

After adjusting the weights based on the errors, method 600 continues to 628. At 628, method 600 may verify the multi-tasking deep neural network with the validation dataset created at 615. Verifying the multi-tasking deep neural network with the validation dataset enables optimization and assessment of the multi-tasking deep neural network, for example by indicating that the number of hidden nodes may be adjusted (e.g., increased or decreased) in one or more hidden layers, or by determining that backpropagation is complete.

After training the multi-tasking deep neural network model by calculating errors and adjusting the weights of each hidden node of the hidden layers based on the errors, method 600 may continue to 629. At 629, method 600 may test the multi-tasking deep neural network with the test dataset created at 615. Testing the multi-tasking deep neural network model with the test dataset enables confirmation that the multi-tasking deep neural network is sufficiently trained to predict multiple health care outcomes with an acceptable error rate.

After training the neural network model with the prepared clinical data, the trained multi-tasking deep neural network may be used to predict multiple health care outcomes. Thus, after training the multi-tasking deep neural network with the prepared clinical data at 620, method 600 continues to 630. At 630, method 600 includes predicting multiple health care outcomes with the trained multi-tasking deep neural network. Predicting multiple health care outcomes may include, at 632, receiving new clinical data for a patient. The new clinical data for the patient may include, as non-limiting examples, historical claims data for the patient, biographical and/or demographic information for the patient, medical test results for the patient, and so on. Continuing at 634, predicting multiple health care outcomes includes inputting the new clinical data to the trained multi-tasking deep neural network. The clinical data may be prepared as discussed above for input to the trained multi-tasking deep neural network.

At 636, predicting multiple health care outcomes includes generating a plurality of outputs with the trained multi-tasking deep neural network based on the new clinical data. At 638, predicting multiple health care outcomes includes outputting the generated plurality of outputs. For example, the generated plurality of outputs may be output to a display device, such as display subsystem 117, for display to a user. Displaying the plurality of outputs may enable a health care provider to better understand an individual's unique comorbidity profile, because it gives more relative context. As an example, it may be helpful to know that an individual is high-risk for an emergency room visit, but it also helps to know at the same time that the individual is at a high risk for cardiovascular disease and is predictive to have low pharmacy monetary expenses.

Additionally or alternatively, in some examples, the generated plurality of health care outcome outputs may be sent to memory, such as computer-readable storage medium 115, for storage, such that the generated plurality of health care outcome outputs may be retrieved for later analysis and/or display. In yet other examples, the generated plurality of health care outcome outputs may be output to another computing system. For example, the generated plurality of health care outcome outputs may be output or transmitted via a communication system, such as communication subsystem 119, to another computing device via a wired or wireless network. Method 600 may then end.

Figure 7:
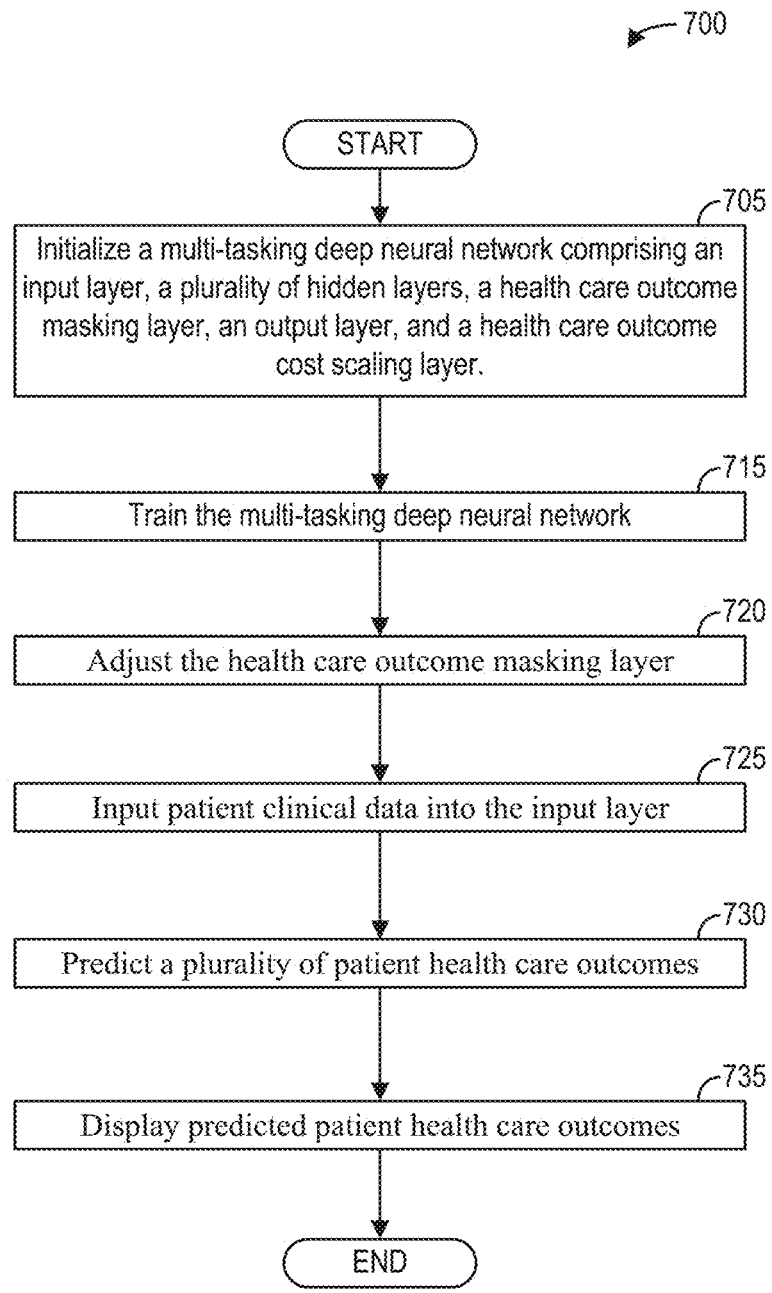
FIG. 7 shows a high-level flow chart illustrating an example method for predicting multiple health care outcomes with a multi-tasking deep neural network.

FIG. 7 shows another high-level flow chart illustrating an example method 700 for predicting multiple health care outcomes with a multi-tasking deep neural network. Method 700 may be carried out, as a non-limiting example, by a computing system such as the computing system described herein above with regard to FIG. 1, though it should be understood that the method may be carried out by other systems without departing from the scope of the current disclosure.

Method 700 begins at 705. At 705, method 700 includes initializing a multi-tasking deep neural network. Initializing the multi-tasking deep neural network includes creating a multi-tasking deep neural network with an input layer including a plurality of inputs, a plurality of hidden layers comprising a plurality of hidden nodes in each of the plurality of hidden layers, a health care outcome masking layer comprising a plurality of masking nodes, an output layer including a plurality of outputs, and a health care outcome cost scaling layer comprising a plurality of cost scaling nodes. Each node or neuron of the layers may be initialized with an initial weight. During training of the multi-tasking deep neural network, the initial weight is adjusted based on the training data, as discussed further herein. Method 700 may then proceed to 715.

At 715, method 700 comprises training the multi-tasking deep neural network using a training dataset comprising training data, validation data, and testing data. Each of the subsets of the training dataset comprise clinical data and corresponding health care outcomes. In one example, clinical data may comprise a medical history of a patient, and a corresponding health care outcome may comprise one or more health care outcomes associated with the patient, wherein the data represent real world data pulled from medical records, medical charts, medical databases etc. Training of the multi-tasking deep neural network may proceed as discussed in more detail above with reference to 620 of method 600 above. Method 700 may then proceed to 720.

At 720, method 700 includes, prior to prediction of a plurality of health care outcomes for a patient, adjusting one or more masking nodes of a health care outcome masking layer of the multi-tasking deep neural network based on a characteristic of the patient. In one example, said adjusting may comprise setting a masking node of the health care outcome masking layer to multiply input received by the node with a factor. In one example the factor is zero, which thereby suppresses output of an associated health care outcome. In another example, the factor is one, thereby not suppressing the output of an associated health care outcome. Said adjusting may be based on a characteristic of the patient for whom a plurality of health care outcomes is to be predicted by the multi-tasking deep neural network. In one example the characteristic is a physical characteristic. As an example, said physical characteristic may comprise one or more of patient age, patient sex, patient race, patient physical condition, or other characteristics of the patient which may indicate that a patient is precluded from susceptibility to one or more health care outcomes. Upon adjusting the masking nodes of the health care outcome masking layer in a manner specific to a characteristic of the patient, method 700 may proceed to 725.

At 725, method 700 comprises inputting patient clinical data into the input layer of the multi-tasking deep neural network. In one example, said inputting may comprise retrieving a medical history of the patient, breaking the medical history into features, and inputting the features into the input layer of the multi-tasking deep neural network. In another example, clinical patient data may comprise ICD diagnosis codes associated with the patient. Method 700 may then proceed to 730.

At 730, method 700 includes predicting at least a first and a second health care outcome for the patient, the first health care outcome predicted based on a first output from a first output node, and the second health care outcome based on a second output from a second output node, wherein both the first and second output are based on the patient clinical data. In one example, the first and the second predicted health care outcome may comprise alternate definitions of a single health care outcome, thereby providing redundancy in prediction which helps reduce a probability that a given health care outcome may be miss predicted based on use of one specific definition. In another example, the first and the second health care outcome may comprise a classification health care outcome, and a related regression health care outcome, such as a prediction of an ER visit (classification health care outcome) and a monetary expense of the ER visit (regression health care outcome). In one example, a third, fourth, fifth, or up to n health care outcomes may be predicted, where n is a positive integer greater than two. In another example, based on the first and the second predicted health care outcome, a medical procedure of the patient may be determined, such as a heart surgery being determined for a patient based on the first and the second predicted health care outcome comprising an ER visit and a heart attack. In another example, based on the first and the second predicted health care outcome, a monetary expense related to the predicted health care outcomes may be determined. In another example, based on the first and the second health care outcome of the patient, a risk category of the patient may be determined. Method 700 may then proceed to 735.

At 735, method 700 may comprise displaying one or more of the first and the second predicted health care outcome via a display, such as via display subsystem 117. Method 700 may then end.

Several embodiments for predicting multiple health care outcomes have been described herein above. In one embodiment, a method includes receiving clinical data relating to a patient, calculating, with a multi-tasking deep neural network model, a plurality of health outcomes for the patient based on the received clinical data, and displaying one or more of the plurality of health outcomes.

In another embodiment, a computer-readable storage medium includes an executable program stored thereon, the program configured to cause a computer processor to retrieve clinical data relating to a patient, process the clinical data using a multi-tasking deep neural network model to calculate a plurality of health outcomes for the patient based on the received clinical data, and display one or more of the plurality of health outcomes.

In another embodiment, a system includes a display device, a user interface device, and a processor communicatively coupled to the user interface device and the display device, the processor configured with a multi-tasking deep neural network model stored in non-transitory memory, the processor further configured with instructions stored in the non-transitory memory that when executed cause the processor to retrieve clinical data relating to a patient, calculate, using the multi-tasking deep neural network model, a plurality of health outcomes for the patient based on the received clinical data, and display one or more of the plurality of health outcomes.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:
    initializing a multi-tasking deep neural network comprising:
        an input layer comprising a plurality of input nodes;
        a plurality of hidden layers;
        an output layer comprising a plurality of output nodes, wherein the plurality of output nodes correspond to a plurality of health care outcomes;
        a health care outcome masking layer comprising a plurality of masking nodes, wherein the health care outcome masking layer is positioned after the plurality of hidden layers; and
        a health care outcome cost scaling layer positioned after the output layer;
    training the multi-tasking deep neural network using a training dataset;
    setting a masking node output of a first masking node of the plurality of masking nodes to zero based on a characteristic of a patient indicating that the patient is not susceptible to a health care outcome corresponding to the first masking node;
    multiplying an input received by a second masking node of the plurality of masking nodes from the plurality of hidden layers by one in response to the characteristic of the patient indicating that the patient is susceptible to a health care outcome corresponding to the second masking node;
    inputting patient clinical data into the input layer;
    predicting at least a first health care outcome and a second health care outcome for the patient, the first health care outcome predicted based on a first output from a first output node, and the second health care outcome based on a second output from a second output node, wherein both the first and second output are based on the patient clinical data; and
    displaying one or more of the first and the second health care outcome.

2. The method of claim 1, wherein the plurality of health care outcomes comprise regression and classification health care outcomes.

3. The method of claim 1, wherein the plurality of output nodes output both classification and regression health care outcomes.

4. The method of claim 1, wherein the plurality of input nodes comprise input nodes configured to receive input of diagnosis codes.

5. The method of claim 1, wherein the characteristic of the patient comprises a physical characteristic of the patient.

6. The method of claim 5, wherein the physical characteristic of the patient comprises a sex of the patient.

7. The method of claim 1, wherein the training dataset comprises training data, validation data, and testing data, wherein each of the training data, validation data, and testing data, comprise clinical data and corresponding health care outcomes.

8. The method of claim 1, wherein the health care outcome cost scaling layer increases a weight of an error of an output node based on rarity of a health care outcome corresponding to the output node.

9. The method of claim 1, wherein the health care outcome cost scaling layer increases a weight of an error of an output node based on a monetary expense associated with a health care outcome, wherein the health care outcome corresponds to the output node.

10. The method of claim 1, wherein the first and the second health care outcome are used to calculate a monetary expense associated with the first and the second health care outcome.

11. The method of claim 1, further comprising based on the predicted first and the second health care outcome, a medical procedure for the patient is determined.

12. The method of claim 1, further comprising outputting one or more of the first and the second health care outcome to one or more of a computer-readable storage medium, and a communication subsystem.

13. The method of claim 1, wherein the first and the second health care outcome comprise alternate definitions of a single health care outcome.

14. A method stored in a computer-readable storage medium of a computing system that when executed by a processor of the computing system performs steps of:
    initializing a multi-tasking deep neural network comprising:
        an input layer comprising a plurality of input nodes;
        a plurality of hidden layers;
        an output layer comprising a plurality of output nodes, wherein the plurality of output nodes correspond to a plurality of health care outcomes;
        a health care outcome masking layer positioned between the plurality of hidden layers and the output layer; and a health care outcome cost scaling layer;

training the multi-tasking deep neural network using a training dataset comprising clinical data and corresponding health care outcomes;

setting a masking node output of a first masking node of the health care outcome masking layer to zero based on a characteristic of a patient indicating that the patient is not susceptible to a health care outcome corresponding to the first masking node;

multiplying an input received by a second masking node of the health care outcome masking layer from the plurality of hidden layers by one in response to the characteristic of the patient indicating that the patient is susceptible to a health care outcome corresponding to the second masking node;

inputting patient clinical data into the input layer;

predicting a plurality of patient health care outcomes based on output from the plurality of output nodes of the output layer; and displaying one or more of the predicted plurality of patient health care outcomes via a display subsystem of the computing system.

15. The method of claim 14, wherein the health care outcome masking layer comprises a plurality of masking nodes corresponding to the plurality of output nodes, wherein responsive to a first masking node outputting zero an output from a first output node corresponding to the first masking node is suppressed.

16. The method of claim 15, wherein responsive to a second masking node outputting one, an output from a second output node corresponding to the second masking node is not suppressed.

17. A computing system comprising:
a display subsystem;
a processor; and
a computer-readable storage medium containing instructions that when executed by the processor perform steps of:
  initializing a multi-tasking deep neural network comprising:
    an input layer comprising a plurality of input nodes;
    a plurality of hidden layers;
    an output layer comprising a plurality of output nodes corresponding to a plurality of health care outcomes;
    a health care outcome masking layer comprising a plurality of masking nodes, wherein the health care outcome masking layer is positioned between the plurality of hidden layers and the output layer; and
    a health care outcome cost scaling layer, wherein the health care outcome cost scaling layer adjusts a weight of an error associated with each of the plurality of output nodes;
  training the multi-tasking deep neural network using a training dataset comprising clinical data;
  setting an output of a first masking node of the health care outcome masking layer to zero based on a physical characteristic of a patient indicating that the patient is not susceptible to a health care outcome corresponding to the first masking node;
  multiplying an input received by a second masking node of the health care outcome masking layer from the plurality of hidden layers by one in response to the physical characteristic of the patient indicating that the patient is susceptible to a health care outcome corresponding to the second masking node;
  inputting patient clinical data into the plurality of input nodes;
  predicting a plurality of patient health care outcomes based on output from the plurality of output nodes, wherein the plurality of patient health care outcomes comprise classification and regression health care outcomes; and
  displaying one or more of the plurality of patient health care outcomes.

18. The computing system of claim 17, wherein regression health care outcomes comprise one or more of:
a duration of inpatient stay;
a monetary expense associated with one or more of the predicted plurality of patient health care outcomes; and
a duration of time until one or more of the predicted plurality of patient health care outcomes.

* * * * *